(12) United States Patent
Oz et al.

(10) Patent No.: US 11,311,190 B2
(45) Date of Patent: *Apr. 26, 2022

(54) SYSTEM AND METHOD FOR MEASURING OCULAR MOTILITY

(71) Applicant: NOVASIGHT LTD., Airport City (IL)

(72) Inventors: Dan Oz, Even Yehuda (IL); Michael Belkin, Givat Shmuel (IL); Oren Yehezkel, Ramat Gan (IL)

(73) Assignee: Novasight LTD., Airport City (IL)

(*) Notice: Subject to any disclaimer, the term of this patent is extended or adjusted under 35 U.S.C. 154(b) by 203 days.

This patent is subject to a terminal disclaimer.

(21) Appl. No.: 16/543,575

(22) Filed: Aug. 18, 2019

(65) Prior Publication Data
US 2020/0107721 A1 Apr. 9, 2020

Related U.S. Application Data

(63) Continuation of application No. 15/550,780, filed as application No. PCT/IL2016/050232 on Mar. 1, 2016, now Pat. No. 10,441,165.
(Continued)

(51) Int. Cl.
*A61B 3/00* (2006.01)
*A61B 3/08* (2006.01)
(Continued)

(52) U.S. Cl.
CPC ............ *A61B 3/113* (2013.01); *A61B 3/0058* (2013.01); *A61B 3/0091* (2013.01); *A61B 3/085* (2013.01); *A61B 3/14* (2013.01); *A61B 3/18* (2013.01)

(58) Field of Classification Search
CPC .......... A61B 3/0058; A61B 3/18; A61B 3/08; A61B 3/085; A61B 3/0025; A61B 3/0041;
(Continued)

(56) References Cited

U.S. PATENT DOCUMENTS 5,550,601 A * 8/1996 Donaldson ............. A61B 3/085
351/209
5,838,420 A * 11/1998 MacGregor Donaldson ...............
A61B 3/113
351/209

(Continued)

*Primary Examiner* — Jordan M Schwartz
(74) *Attorney, Agent, or Firm* — The Law Office of Joseph L. Felber

(57) ABSTRACT

The present invention provides a system and a method for measuring ocular motility of a patient. The system comprises a display unit capable of presenting at least one target; a blocking unit configured and operable to selectively block/unblock at least one target in a field of view of at least one eye of the patient; a camera unit comprising at least one imaging element configured and operable to generate at least two image data indicative of at least one eye condition; and a processing unit connected to the blocking unit, to the display unit and to the camera unit, the processing unit being configured for performing the following steps: (a) displaying at least one target, for at least one eye (b) receiving image data indicative of at least one eye's condition from the camera unit, (c) controlling the blocking unit to block/unblock at least one target in the field of view of at least one eye of the patient, (d) detecting a change in at least one eye's condition, (e) displacing the target for at least one eye; and repeating steps (a)-(e) until no change in the eye's condition is measured to thereby determine at least one ocular motility parameter.

5 Claims, 11 Drawing Sheets

Related U.S. Application Data

(60) Provisional application No. 62/126,622, filed on Mar. 1, 2015.

(51) Int. Cl.
*A61B 3/14* (2006.01)
*A61B 3/18* (2006.01)
*A61B 3/113* (2006.01)

(58) Field of Classification Search
CPC ......... A61B 3/0091; A61B 3/10; A61B 3/113; A61B 3/14
See application file for complete search history.

(56) References Cited

U.S. PATENT DOCUMENTS

| | | | |
|---|---|---|---|
| 10,441,165 B2* | 10/2019 | Oz | A61B 3/0091 |
| 2015/0109578 A1* | 4/2015 | Baranton | A61B 3/1035 |
| | | | 351/205 |
| 2015/0243036 A1* | 8/2015 | Hoffmann | G06T 7/75 |
| | | | 382/103 |
| 2016/0000317 A1* | 1/2016 | Krall | G06F 3/013 |
| | | | 351/240 |
| 2017/0007119 A1* | 1/2017 | Cornsweet | A61B 3/112 |
| 2017/0311793 A1* | 11/2017 | Green | A61B 3/113 |
| 2019/0046029 A1* | 2/2019 | Tomasi | A61B 3/10 |

\* cited by examiner

View a-a

View c-c        View b-b

SYSTEM AND METHOD FOR MEASURING OCULAR MOTILITY

TECHNOLOGICAL FIELD

The present invention relates to ophthalmology and more specifically to a technique used in routine and specialized diagnosis, measurements and monitoring of ocular motility, binocular alignment and other visual functions.

BACKGROUND

Both eyes of a healthy individual are aligned and the visual axes are parallel under most viewing conditions. Deviation from this state may cause diplopia. Strabismus is a visual disorder in which the eyes are misaligned. Strabismus. (i.e. double vision), which is present in about 4% of children in the U.S., prevents stereopsis (i.e. depth perception) and can lead to development of amblyopia (i.e. lazy eye). Amblyopia is a decrease in vision in one or both eyes that cannot be accounted for by any structural abnormality and cannot be treated by optical devices. Amblyopia can be engendered by childhood strahismus, as a result of the child's brain ability to disregard the image from the deviating eye, in order to avoid double vision. If this condition is not treated in early childhood the amblyopia might become permanent.

Eye misalignments are classified to subtypes with different clinical implications. A major factor is whether the eyes deviate constantly (i.e. Heterotropia) or only under certain circumstances (i.e. heterophoria). The latter may lead to eye fatigue, reading disorders and decrements in stereopsis, but not for amblyopia. Lntreated heterotropia leads to amblyopia in most cases when one eye is constantly deviating. In strabismus, there may be a cosmetic blemish if the angle between the visual axes is large enough.

As with other binocular vision disorders, the primary therapeutic goal for strabismus is a comfortable, single, clear, normal binocular vision at all distances and directions of gaze. Strabismus is usually treated with a combination of eyeglasses and surgery.

The earlier the treatment of strabismus is initiated in infancy, it is less likely to develop amblyopia. Starting treatment at as young an age as possible may ensure the development of the best possible visual acuity in both eyes and enable stereopsis. Strabismus is generally treated by preventing good vision in the non-deviating (non strabismic) eye, by physical, pharmacology or optical blurring. The treatment of amblyopia does not change the angle of strabismus which, if large enough, is treated surgically.

A patient with a constant deviation eye turn of significant magnitude, is very easy to notice. However, a small magnitude or intermittent strabismus can easily be missed upon casual observation.

Adults might also develop strabismus; they usually do not develop amblyopia, but a double vision. Except for the discomfort of double vision, people of all ages may experience psychosocial difficulties if they have noticeable strabismus. Successful surgical correction of strabismus has positive effects on psychological well-being, even when implemented with adult patients. Although not a cure for strabismus, prism lenses can also be used to provide comfort for patients and to prevent double vision from occurring. The prisms can usually enable single vision in only single gaze position since the angle between eyes might change according to the visual gaze direction.

Thus early detection of strabismus in young children is of paramount importance in avoiding amblyopia and increasing the chances of developing proper binocular vision. Determining the origin, the type and the angles of strabismus is important for treatment decisions such as which of the external eye muscles to operate, and to what degree.

There exist several strabismus and ocular motility examinations as follows:

Pupillary light reflex examination, in which a patient is directed to look at a point of light held a meter away. If the light reflections are located symmetrically in each pupil, the eyes are parallel. Asymmetric reflections indicate possible strabismus. The angle of the deviation may be measured by bringing the reflection to symmetry by a prism of appropriate strength. However, this test is inaccurate, but is the only one possible in most babies.

A cover test is performed while the patient looks at a near or distant target, and one eye is covered, while the uncovered one observes. The patient is required to fixate on a target while the examiner repeats the test several times using prism lenses with a variety of strengths and directions (up, down, in and out) in order to measure the misalignment parameters. This procedure might take a long period of time, up to 30 minutes when testing infants or toddlers. Asking young children to cooperate and fixate for such a long time is challenging and requires the specialist to be very creative.

A prism cover test, in which the degree of eye misalignment is established by neutralizing the uncovered eye movements using a prism bar or prism lenses. This test should be performed separately for horizontal and vertical strabismus. However, this test requires a patient's cooperation and is quite complicated to perform.

The cover and prism cover tests require the subjective judgment of the specialist to determine the existence of eye movements between consecutive cover/uncover steps.

There are also further complicated tests such as tests using a Hess screen which are also subjective, more complicated, and which are time consuming.

All the above tests are complicated to perform and are imprecise, prolonged, and have to be performed by a specialist. Furthermore, they are difficult, and in many cases impossible to perform on infants and toddlers.

General Description

The present invention provides a system and method for measuring ocular motility being an objective test that does not depend on subjective feelings of a specialist or the patient, needs minimal cooperation of the patient, and automatically provides results, even when performed by a technician. The technique of the present invention provides each eye with its own target and moves each target on a screen independently and respectively for each eye to thereby determine ocular motility parameters such as strabismus deviation for near field, strabismus deviation for far field, abnormal torsion tilt of an eye, heterotropia, heterophoria, nystagmus, eye movements and fusional reserves.

According to a broad aspect of the present invention, there is provided a system for measuring ocular motility of a patient, the system comprising a display unit capable of presenting at least one target; a blocking unit configured and operable to selectively block/unblock at least one target in a field of view of at least one eye of the patient; a camera unit comprising at least one imaging element configured and operable to generate at least two image data indicative of at least one eye condition, and a processing unit connected to the blocking unit, to the display unit and to the camera unit, the processing unit being configured for performing the following steps: (a) displaying at least one target, for at least one eye (b) receiving image data indicative of at least one eye's condition from the camera unit. (c) controlling the blocking unit to block/unblock at least one target in the field of view of at least one eye of the patient. (d) detecting a change in at least one eye's condition, (e) displacing the target for at least one eye; and repeating steps (a)-(e) until no change in the eye's condition is measured to thereby determine at least one ocular motility parameter.

It should be understood that the technique of the present invention determines ocular motility parameter by measuring a change in the eye's condition, if any, and not its absolute position parameters. This novel technique eliminates the need for calibration, which usually has to be done in commercially available devices for ocular motility parameter measurements, because the camera unit does not provide precise information data regarding the position of the eye. The information needed for the novel procedure is the occurrence of a movement/no movement of the eye. A precise location of each eye is not necessary for identifying any differences between the eyes' gazing directions.

The technique of the present invention is less complicated than existing procedures, reduces the need for subjective assessment by a specialist, is nearly automatic, is relatively fast, and reduces the need for patient cooperation which is challenging, especially for young children. The present invention is able to measure several dysfunctioning types of ocular motility such as strabismus, eye movements.

Heterophoria, cranial nerve palsies, cyclotropia, cyclophoria, nystagmus, fusional reserves etc. In this connection, it should be noted that in some kinds of strabismus, not one deviating eye exists, and the gazing direction of the patient can be done alternatively by both eyes. The ability of the system to provide separate images for separate eyes together with the displacement of the targets, enables to determine different ocular motility parameters.

It should be understood that if there is no strabismus, the uncovered eye will not move. In the presence of strabismus, covering the non deviating eye leads to change in position of the deviating, uncovered eye as it moves to fixate upon the target. Covering the deviating, strabismic eye will lead to no movement of the other, non deviating eye, since this eye gaze is directed toward the target.

In some embodiments, the blocking unit is configured and operable to selectively block/unblock a field of view of at least one eye.

In some embodiments, the camera unit is configured and operable to generate consecutively at least two image data indicative of at least one eye condition. The comparison is performed by comparing two images taken at different times.

In some embodiments, the eye conditions comprise at least one of horizontal gazing direction, vertical gazing direction and rotational axis. The eye conditions may also comprise at least one parameter of a trajectory of at least one eye during the procedure of steps (b)-(e). At least one parameter of the trajectory may comprise at least one of horizontal gazing direction, vertical gazing direction and torsional rotation, velocity (also called gazing shift speed) and acceleration. It should be noted that for measuring eso, exo, up or down tropia, gazing direction is measured, for torsional strabismus (Cyclotropia), the rotational axis is measured.

The parameters of the trajectory describe the physical movement of the eye in space, and enable the option to provide a patient's condition e.g. what muscle or nerve, if any, might be impaired.

The system may be used under monocular and/or binocular and/or dichoptic vision. When the system is monocular, one target is presented to one eye. When the system is binocular, one target is presented to both eyes. When the system is dichoptic, two separate targets, with similar (or even identical) or different shape, placed either spaced apart or at the same location, are presented.

The processing unit may thus be configured for performing the following initialization step presenting two targets, one for each eye, at the same location.

In some embodiments, the blocking unit may comprise at least one of glasses, screen and projector. The blocking unit may be activated actively or passively. If activated actively, the blocking unit may comprise an alternating shutter for instance, configured for covering the image of each eye alternatively. If the blocking unit is a passive type, it may comprise passive polarized filters or passive anaglyph filters for instance.

In some embodiments, the display unit is activated actively or passively. The display unit may comprise a video display. The display unit may be capable of presenting at least two images of the same target, or two images of two different targets.

In some embodiments, the display unit comprises a 3-Dimensional (3D) display unit e.g. a screen capable to provide at least two separate images, one for each eye.

In some embodiments, the blocking unit is connected to the display unit.

In some embodiments, the processing unit displaces the target in at least one of the following displacement manners: horizontally, vertically and rotationally. Displacement of the target can be made according to a predefined trajectory or for an eye respectively to the target of the second eye. The targets may be placed in close proximity, or may be moved away.

In some embodiments, the system comprises a head tracker configured for detecting at least one of head location, direction and movement to thereby enable determining ocular motility parameters for different gazing directions. The system may also comprise multiple displays. The technique is thus able to measure ocular motility parameters in different head positions and different gazing directions, and provides at least one of vertical, horizontal and torsional deviations tests of at least one eye in a fast manner.

In some embodiments, the system comprises optical corrective lenses.

In some embodiments, the camera unit comprises a video camera.

In some embodiments, the camera unit comprises an eye tracker.

According to another broad aspect of the present invention, there is also provided a method for measuring ocular motility of a patient, the method comprising the following steps: (a) displaying at least one target for both a first and second eye; (b) collecting at least one image data indicative of at least a first eye's condition; (c) determining a first condition of the first eye; (d) blocking the target in a field of view of the second eye; (e) collecting at least one image data indicative of a second condition of the first eye; (f) determining a second condition of the first eye; (g) identifying an existence of an eye movement and determining whether there is a change in the condition; (h) if a change is determined, unblocking the field of view of the second eye, displacing the target for the first eye, and unblocking the field of view of the second eye; and; (i) repeating steps (b)-(h), until no change in the condition of at least the first eye is measured.

It should be noted that this procedure can be applied to a specific eye of a patient, if pretest information has been received about a specific deficient eye. Otherwise, the procedure is applied randomly to each eye and if no change is determined in step (i) for a first eye, steps (b)-(j) are repeated for the second eye.

In some embodiments, the method comprises comparing between the image data indicative of the second and the first eye's conditions to thereby determine whether there is a change in the eye's condition.

In some embodiments, the method comprises measuring the distance between the two targets of the two eyes on the display and/or the distance of eye to display to thereby determine at least one ocular motility parameter of the first eye.

It should be noted that since the method of the present invention may use the measure of the distance between the two targets presented on the display unit to evaluate misalignment of the deviating eye, the image of the non-deviating eye can be shifted/displaced toward the eye gaze (in a case of the patient who has changed his gaze). Thus, the target position of the deviating eye may be compensated for the shift of the undeviating eye toward the same direction. Alternatively, the system can hold or even eliminate the procedure in case the patient is not looking at the target or closing the eyes.

According to another broad aspect of the present invention, there is provided a method for measuring ocular motility parameters by presenting at least two targets creating a virtual target at a required distance from the patient. In this way, the system of the present invention is capable to be adapted to any distance and therefore is able to perform measurement for far field as well as near field without changing the patient-display distance. The certain focal point may be varied to thereby enable keeping a distance between a display unit and a patient to be fixed, while varying the virtual target distance. The distance between the virtual target and the patient's eye may be varied by displacing the targets with respect to each other (closer or farther) along the display unit.

The distance between the targets can be selected to correspond to an interpupillary distance of the patient. A distance between a display unit (configured to display the targets) and a patient can be selected to be in the range, for example, of about 30 cm to 700 cm.

In some embodiments, the method comprises controlling the accommodation state of the eyes by providing focusing optics.

In some embodiments, the method comprises displacing the relative locations of the two targets leading to eye convergence in order to present a virtual target at a selected distance. According to another broad aspect of the present invention, there is provided a system for measuring ocular motility of a patient, the system comprising a display unit capable of presenting at least two targets independently to each eye; a blocking unit configured and operable to selectively block/unblock at least one target in a field of view of at least one eye of the patient; a camera unit comprising at least one imaging element configured and operable to generate at least two image data indicative of at least one eye condition; a processing unit controlling the blocking unit, the display unit and the camera unit; and a focusing optics placed in front of the eyes, connected to the display unit; and being configured and operable to receive an image from the display unit and project the image to each eye in such a way so that the eye sees the target at a required distance. The focusing optics is configured to create a virtual target located at any required distance. Therefore, the focusing optics is configured and operable to change the virtual distance between the target and the patient.

In some embodiments, the focusing optics comprises at least two optical lenses having a certain focal point. The lenses may be convex or concave lenses.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
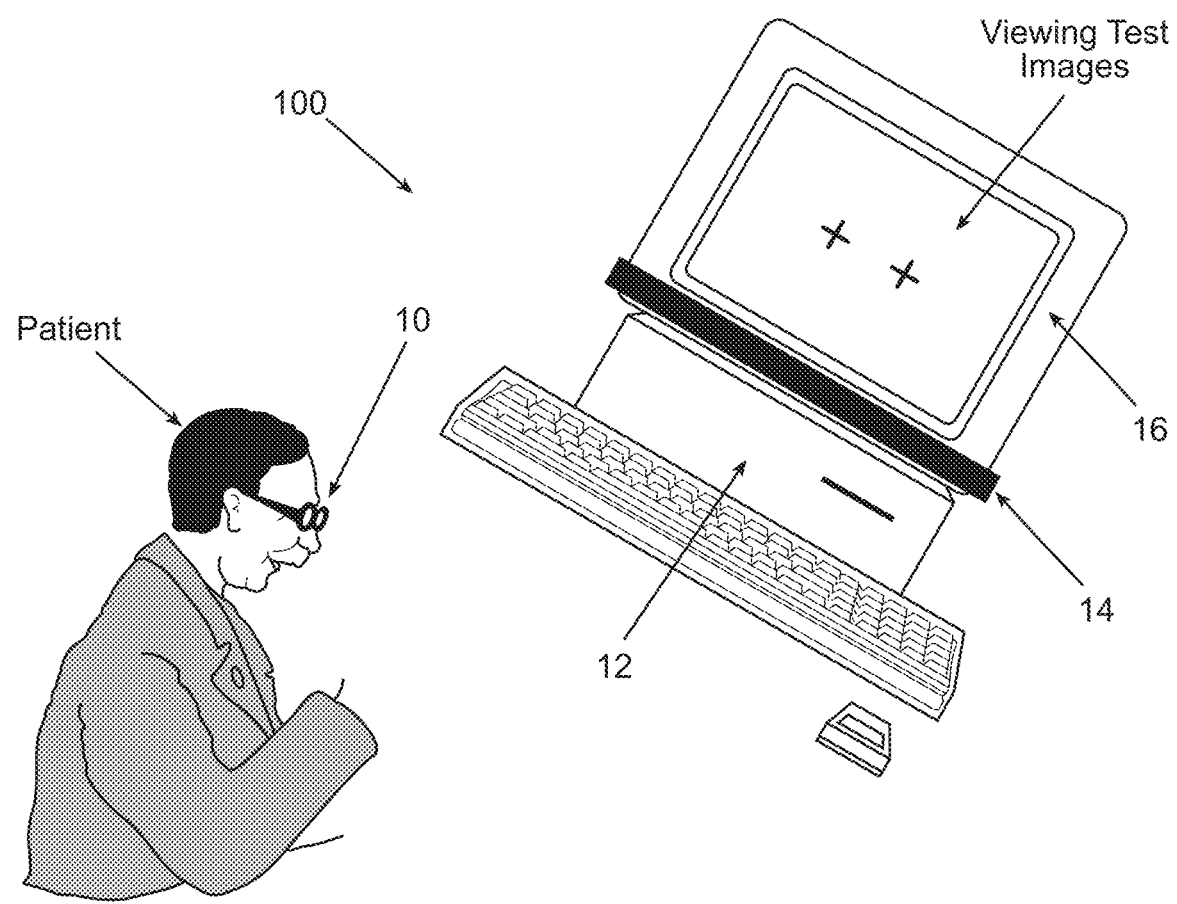
FIG. 1 represents a schematic example of a possible configuration of the system of the present invention.

Reference is made to FIG. 1, schematically representing the system 100 according to some embodiments of the present invention. In the figure, the system 100 comprises a display unit 16 presenting two targets; a blocking unit 10 configured and operable to selectively block/unblock a field of view of at least one eye of the patient; a camera unit 14 configured and operable to generate at least two image data indicative of at least one eye condition; and a processing unit 12 connected to the blocking unit 10, to the display unit 16 and to the camera unit 14. The processing unit is configured for controlling the blocking unit 10 to block/unblock the field of view at least one eye of the patient, receiving image data indicative of at least one eye's condition from the camera unit, measuring a change in the eye condition, visually displacing the target on the display unit and determining at least one ocular motility parameter. The display unit is thus 16 capable of presenting at least two targets. The display unit 16 may be configured and operable to present separate targets to each of the eyes. The two separate targets can be displayed either sequentially or simultaneously. The display unit 16 may be an active or passive 3D type. In an active 3D display, presentation of the two targets is sequential. In a passive 3D display, presentation of the two targets is not sequential, hut simultaneous. It should be noted that although in the figure the target is represented as a cross, it can have any geometrical shape, to be either constant or dynamic, aimed at determining the ocular motility parameters of the patient. The attracting target can be a geometrical figure or a text having the capability to move across the display unit 16 (e.g. a personal computer monitor). The geometrical shape of the target is selected according to the ocular motility parameters examined by the system. For example, the target may comprise a letter or a picture design according to the Snellen or ETDRS charts configured to be calibrated according to the distance between the display and the patient.

In this specific and non-limiting example, the blocking unit 10 is configured to be worn by the patient and is in the form of alternating shutter glasses.

Moreover, although, for the sake of simplicity, the display unit 16 and the blocking unit 10 are represented as two separated elements, they may be integrated in the same housing. In this case, two independent inputs are received by the integrated unit. The display unit 16 can be therefore of autostereoscopy type (glasses free 3D) or it can be screen compatible with 3D glasses. The display unit 16 may also be a wide field of view (FOV) stereographic display or non-stereographic display such as a video projection. If the display unit 16 is a projection device, the image information may be projected by suitable image-producing devices and projection devices on the screens placed before the eyes of the person using the device. The display unit 16 is configured to provide the necessary images for the patient for each eye. Each eye sees only the images intended to be viewed by that particular eye. For example, if polarized glasses are used, an appropriate polarized 3D display has to be used too. These systems are commercially available. Dimenco BV and HR3D from MIT's Media Lab are examples of commercially available glasses free 3D. ASUS VG236H LCD monitor and BenQ XL2410T LCD monitor are examples of monitors compatible with active 3D glasses.

This embodiment includes any of the many approaches for providing separate images to separate eyes. This includes but is not limited to color separated glasses (e.g., the old red and green/blue 3-D glasses), polarization separated glasses, shutter glasses, eye-individualized near-eyes displays and direct projection to individual eye display. Therefore, in some embodiments, the blocking unit 10 comprises alternating shutters, polarized lenses, red/green lenses which may be incorporated in glasses (e.g. test goggles), that can be of a type commercially available and used in 3D videos. Nvidia 3D glasses are an example of commercially available active shutter and RealD XLS by Sony is an example of a commercially available polarized system. The blocking unit 10 may also be of a single polarization type blocking only polarized images, such that only polarized images from the display unit are blocked to enter the eye, hut non-polarized light is allowed to enter the eye.

In some embodiments, the blocking unit 10 is designed to be snug fitting to the patient's face in order to exclude extraneous light, allowing testing to be performed under ordinary room light conditions. The blocking unit 10 is operable to act as an electronic shutter by blocking the gaze of one or the other eye during examination. For example, the blocking unit 10 may comprise two spaced-apart clear liquid crystal panels extending across the visual axis of each eye and being actuated by an electrical signal from the processing unit 12. In a specific and non-limiting example, the shutter panel is round in shape and mounted within the blocking unit 10 at eye level. The panel is divided into a right and left half that can be made transparent or opaque separately for each eye under the processing unit's control.

In some embodiments, the blocking unit 10 alternatively occludes one patient's eye, or one of the eye's targets. The images may be dimmed or blanked for certain periods of transmission and periods of closure determined by the processing unit 12. To this end, the blocking unit 10 may comprise computer controlled shutter panels which occlude the patient's vision in either eye during the testing sequence. Thus, the blocking to unit 10 may comprise an LCD display and may be operated as follows: the polarized image coming from the LCD display can be shut off. Alternatively, the entire field of view can be shut off by the goggles.

In some embodiments, the blocking unit 10 comprises corrective lenses. If the patient has visual acuity that needs to be corrected, such correction can be added to the system as a separate element (mounted on some glasses or placed in front of the patient) or to the near eye blocking unit.

The blocking unit 10 and the display unit 16 are connected by wire or wireless communication and may be synchronized. It is not shown in detail, hut should be appreciated that signal exchange and communication is enabled between the units of the system by virtue of appropriate wiring, or wirelessly. For example, the blocking unit 10 and the display unit 16 can be connected by IR (Infra-Red), RF (radio frequency including Bluetooth) or cable control. The camera unit 14 is connected to a processing unit 12 by wire or wireless communication and is configured to record the eyes' conditions and provide this image data to the processing unit 12. The processing unit 12 measures changes in the images received from the camera unit 14 from step to step while the eyes are alternatively occluded, or by covering and uncovering one of the eyes and the target is displaced. The processing unit 12 may determine the direction of eye movements and may determine a change in the direction of eye movements by comparing sequentially acquired image data.

It should be noted that all required processing operations (such as receiving an image data, determining a gazing direction, selectively occluding an eye, comparing between gazing directions, determining a change in the gazing direction, displacing the target, measuring displacement of the target, repeating the different steps, determining at least one ocular motility parameter), may be performed by means of a processing unit 12, such as a DSP, microcontroller, FPGA, ASIC, etc., or any other conventional and/or dedicated computing unit/system. The term "processing unit" should be expansively construed to cover any kind of electronic device with data processing capabilities, including, by way of non-limiting example, personal computers, servers, computing systems, processors (e.g. digital signal processor (DSP), microcontrollers, field programmable gate array (FPGA), an application specific integrated circuit (ASIC), etc.), smart phone, tablet and other electronic computing devices. The processor unit 12 may comprise a general-purpose computer processor, which is programmed in software to carry out the functions described herein below. Although processing unit 12 is shown in FIG. 1, by way of example, as a separate unit from the camera unit 14, the display unit 16 and the blocking unit 10, some or all of the processing functions of processing unit 12 may be performed by suitable dedicated circuitry within the housing of the camera unit 14 and/or the housing of the display unit 16 and/or the housing of the blocking unit 10 or otherwise associated with the camera unit 14 and/or the display unit 16 and/or the blocking unit 10. Unless specifically stated otherwise, as apparent from the following discussions, it is appreciated that throughout the specification discussions utilizing terms such as "processing", "computing", "calculating", "determining", "comparing", or the like, refer to the action and/or processes of a computer that manipulate and/or transform data into other data, the data represented as physical, e.g. such as electronic, quantities. Also, operations in accordance with the teachings herein may be performed by a computer specially constructed for the desired purposes or by a general purpose computer specially configured for the desired purpose by a computer program stored in a computer readable storage medium. The processor unit 12 includes inter alia at least one utility part (suitable software and/or hardware) for processing the image data and controlling the blocking unit and the display unit. The utility may be preprogrammed to determine a gazing direction, to compare between different image data to thereby determine whether there is a change in the gazing direction, to control the blocking unit to selectively occlude the different eyes, to control the display unit to display and displace the target on the screen, to repeat the steps until no change in the gazing direction is determined, to measure the displacement of the target, and to determine at least one ocular motility parameter. The software may be downloaded to processing unit 12 in electronic form, over a network, for example, or it may alternatively be provided on tangible media, such as optical, magnetic, or electronic memory media. Alternatively or additionally, some or all of the functions of the processing unit 12 may be implemented in dedicated hardware, such as a custom or semi-custom integrated circuit or a programmable digital signal processor (DSP).

Figure 2A:
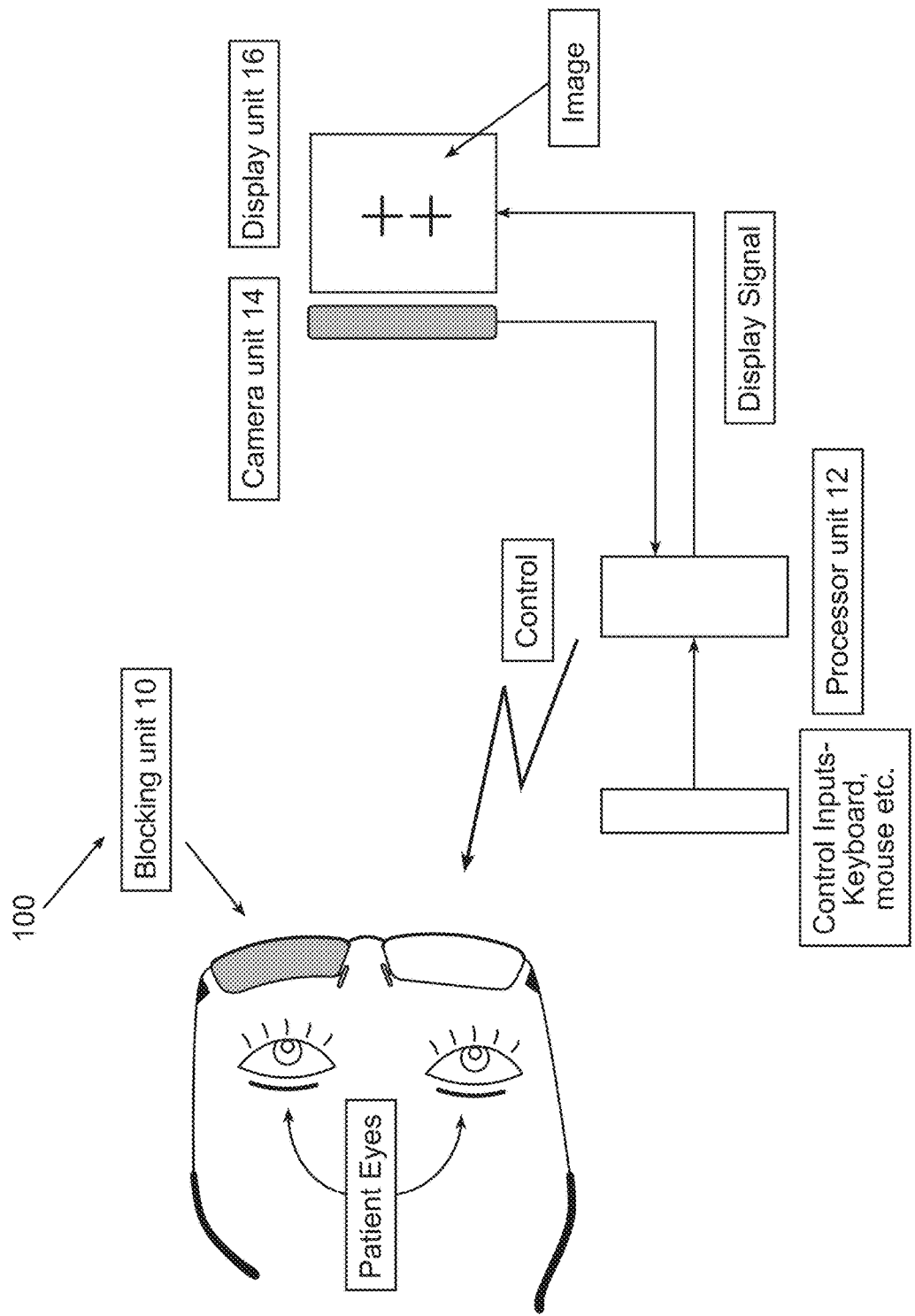
FIG. 2a represents a schematic block diagram of a possible configuration of the system of the present invention.

Reference is made to FIG. 2a, illustrating a block diagram of the system 100 described in FIG. 1 above according to some embodiments of the present invention.

In a specific and non-limiting example, each patient's eye movements were recorded with a camera unit 14 of the type Eyelink 1000 eye tracker. The patient sits in an adjustable height chair. Alternatively, the patient may sit in either a height adjustable or height-fixed chair, with the camera unit height adjusted to the patient. At the first stage, the target video is displayed continuously presenting two targets simultaneously, one for each eye, at the same location on the screen (enabling binocular viewing). A round target is presented, occupying an area of, for example, approximately 1 degree (diameter of 1.7 cm at 100 cm distance). The camera unit 14 may comprise at least one imaging device which generates image data indicative of the eye condition (e.g. gaze direction) or may comprise a commercially available eye tracker. It should be noted that hereinafter the term "camera" refers to any imaging device capable of producing a digital image or video. The camera unit 14 generates image data indicative of an eye condition comprising at least one of horizontal gazing directions, vertical gazing directions and torsional rotations of the eyes. Torsional rotations can be detected by commercially available eye tracker of the type made by Arrington Research. Inc., 27237 N. 71st Place. Scottsdale, Ariz. 85266, USA. In this connection, it should be noted that eye trackers are not often used because of the complicated software and procedures required for calibration, tracking and analyzing of eyes' data. However, to determine ocular motility parameters, the technique of the present invention does not require an accurate calibration since it does not rely on the accurate eyes position in the space, but measures the difference between two consecutive eye gazes by monitoring changes in eye's positions. Therefore, a simple camera or video camera connected to a preprogrammed processing unit can be used instead of an eye tracker. The camera unit 14 may thus be a commercial high-speed camera optionally having an integrated processing unit (appropriate software). The processing unit determines pupil direction by measuring the relative position of the pupil with respect to eye position at high frame rates, such as a video-based corneal reflection unit, available from ISCAN. Thus the processing unit analyzes the gaze direction and other eye data. This part of the processing unit can be a part of a processor located within the camera case (e.g. eye tracker) or this part is a part of the main processor.

Figure 2B:
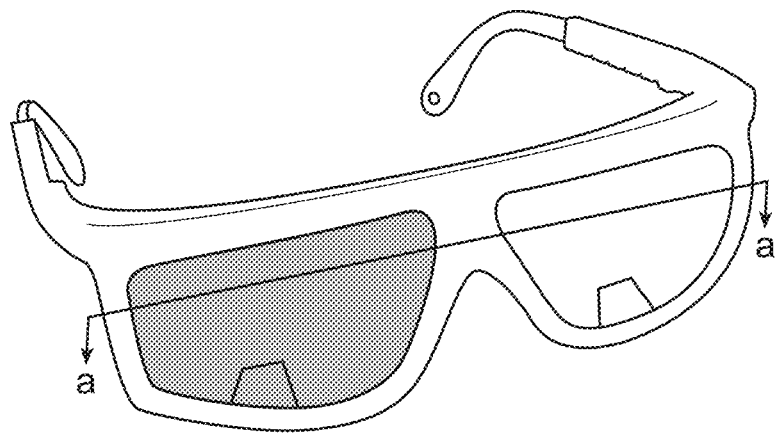
FIG. 2b represents a schematic example of a blocking unit according to some embodiments of the present invention.
Figure 2B:
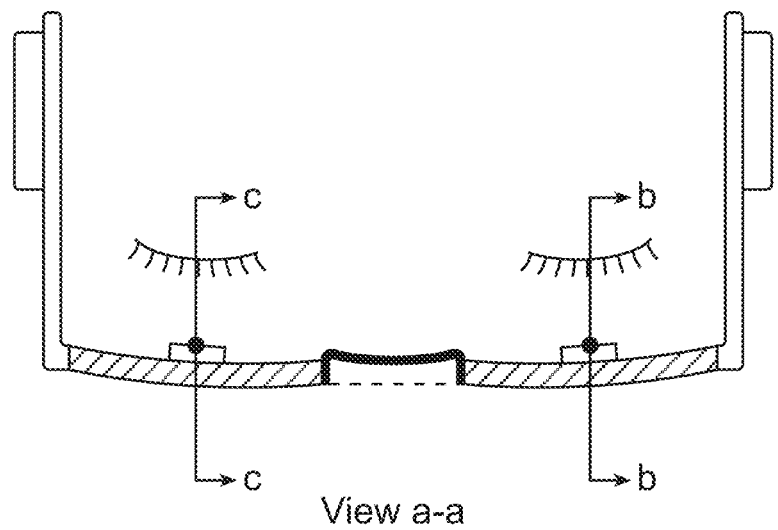
Figure 2B:
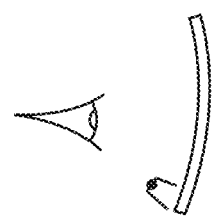
Figure 2B:
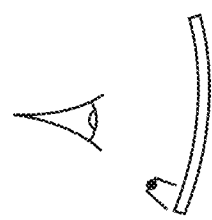

In some embodiments the camera unit 14 is binocular wherein each of the binocular video eye trackers is composed of a miniature camera and infrared light sources, with the dual optics assemblies connected to the processing unit. The camera captures images of the eyes reflected by a dichroic mirror placed behind a head mounted display set of lenses. In some embodiments of the system, an IR source is used for illumination of the user's eye in infrared and imaging the user's eye in the IR range. In some embodiments, the system also includes a head tracker. The camera unit 14 may be located adjacent to the display unit 16 (e.g. remote eye trackers) or fitted on the blocking unit 10 (e.g. near eyes eye trackers). Reference is made to FIG. 2b illustrating an example in which the camera unit 14 is located in the glasses of the blocking unit 10 themselves. For example, when the blocking unit 10 comprises polarization or shutter glasses, a tiny camera may be placed for each eye in the frame of the glasses and serves as a camera of the eye tracker. Thus, at once, the patient sees selective images for each eye and the processing unit (not shown), which typically controls the display unit, also simultaneously receives data indicative of the gaze direction where each eye is looking responsive to the individual images.

In some embodiments, the eye conditions comprise the velocity of at least one eye. This can be achieved for example by acquiring images under occluded/non-occluded conditions. Gazing shift speed can be measured, for example, by bouncing the target and measuring the time that it takes for the eye to reach the new target location, or the time it takes for the strabismic eye to return to its original position after uncovering the non strabismic eye. Furthermore, the processing unit (not shown) can measure the trajectory of the eye between these two positions, whether it is a straight or a curved line. Thus, the technique of the present invention measures ocular motility of a patient and enables to determine which muscle or nerve is impaired, if any. The ocular motility of a patient may also provide objective, accurate information to a practitioner before any surgical intervention.

In some embodiments, the camera unit 14 generates heterophoria data by collecting an image data of the eye during both in occluded and non-occluded states while alternately covering the two eyes. In case of complete visual field occlusion, the camera unit 14 can be located close to the eye, behind the blocking unit 10. As a result, the processing unit simultaneously detects a gazing direction change of both the occluded and non-occluded eyes. It should be noted that, while the blocking unit eliminates the presentation of a polarized image on the display unit, the camera unit tracks the eyes even if the blocking unit occludes the field of view of the eye, since the camera unit receives the reflections from the eyes which are not polarized. When the camera unit 14 is located adjacent to the display unit and the blocking unit is of a single polarization type, non-polarized IR light entering the eye is reflected from the eye and collected by the camera unit 14.

In some embodiments, the camera unit 14 comprises two cameras providing two digital images.

Reference is made to FIGS. 3a-3e illustrating different steps of a method of measuring ocular motility parameters by using a specific configuration of FIGS. 1 and 2 of the system of the invention for patients having exotropia—also referred to as divergent squint—a form of strabismus where an eye is deviated outwards. In such cases, it may be assumed that the right eye is non strabismic, and this eye usually fixates on the image.

Figure 3A:
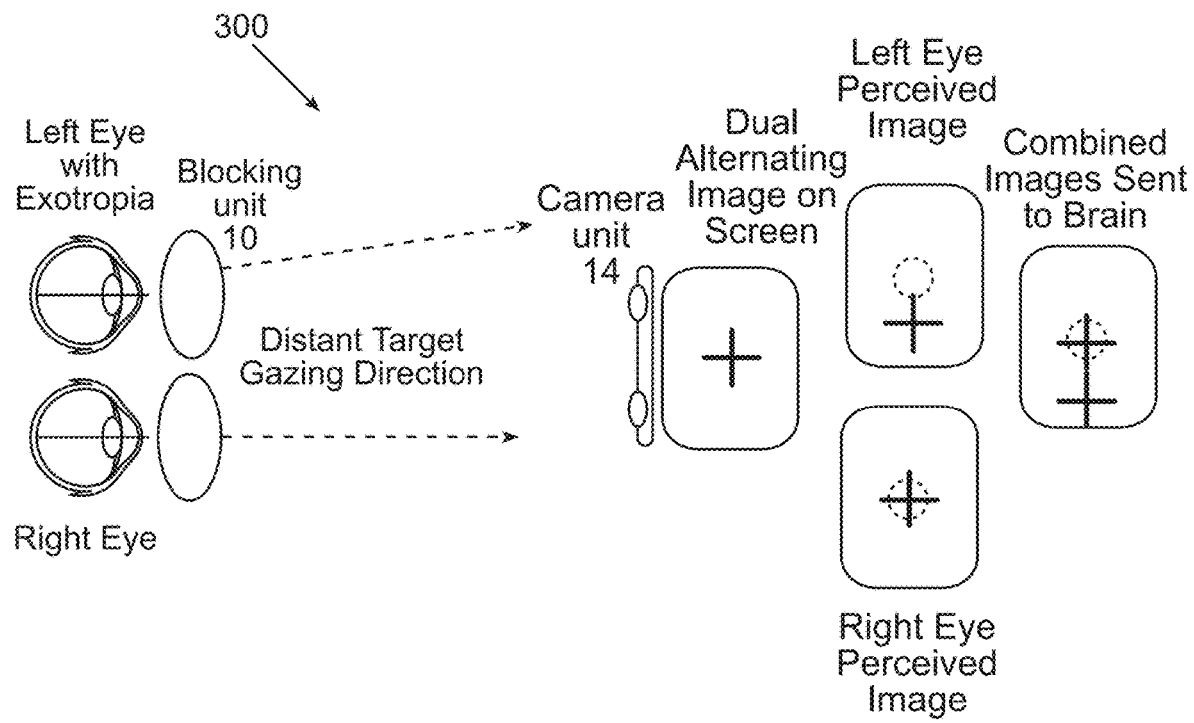
FIG. 3e-3e illustrate different steps of a method of measuring ocular motility parameters by using a specific configuration of the system of the present invention.

In step 1, illustrated in FIG. 3a, two test targets, one for each eye, coincide on the display unit center and both shutters of the blocking unit 10 are transparent. Because of the exotropia (the left eye points outwards), the perceived image of the left eye is not centered on the fovea but rather inwards nasally, as illustrated in the figure. The perceived image of the right eye is centered on the fovea as illustrated in the figure. Patient perception may result in one of the following scenarios: either the brain ignores the image of the left eye and the patient sees only one monocular image, or the patient suffers from diplopia (i.e. double vision). The camera unit 14 generates at least one image indicative of the tested eye position (the right eye). No eye movements are detected by the processing unit (not shown).

Figure 3B:
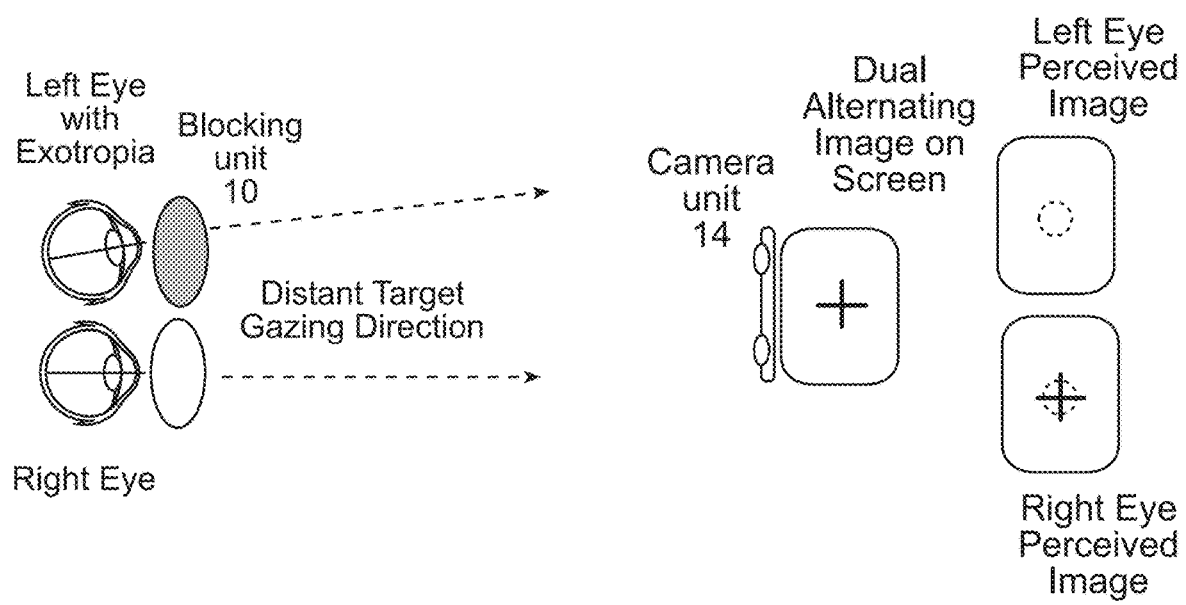

In step 2, illustrated in FIG. 3b, two separate test targets continue to be displayed and coincide on the display unit 16. The blocking unit 10 becomes opaque for the left 34) eye and prevents the left eye from seeing the target. Because of exotropia, the left occluded eye continues to point outwards and the right eye continues to fixate on the right target and produces the perceived target shown in the figure. The camera unit 14 generates image data for the right eye and the processing unit (not shown) compares this image data to the previous image data acquired in step 1. If there is no change in the data for the right eye, this determines that the right eye is the non strabismic eye. If there is a change in the data for the right eye, this determines that the right eye is probably the deviated eye. In the following steps, it may be assumed that the right eye is the non strabismic eye. It should be noted that steps 1 and 2 above are performed solely for determination of the non strabismic eye. These steps art optional and can be eliminated if information regarding non strabismic and leading eye is received in advance. For detecting alternating strabismus, it is required to monitor the eye that moved after the other eye occlusion 0.1 its gazing position does not change after removing the occlusion, this means that the strabismus is alternating. The results should be the same, repeating the test in the other eye. Steps 3 and 4 illustrated in FIG. 3c and FIG. 3d are the actual measurements of strabismus deviation.

Figure 3C:
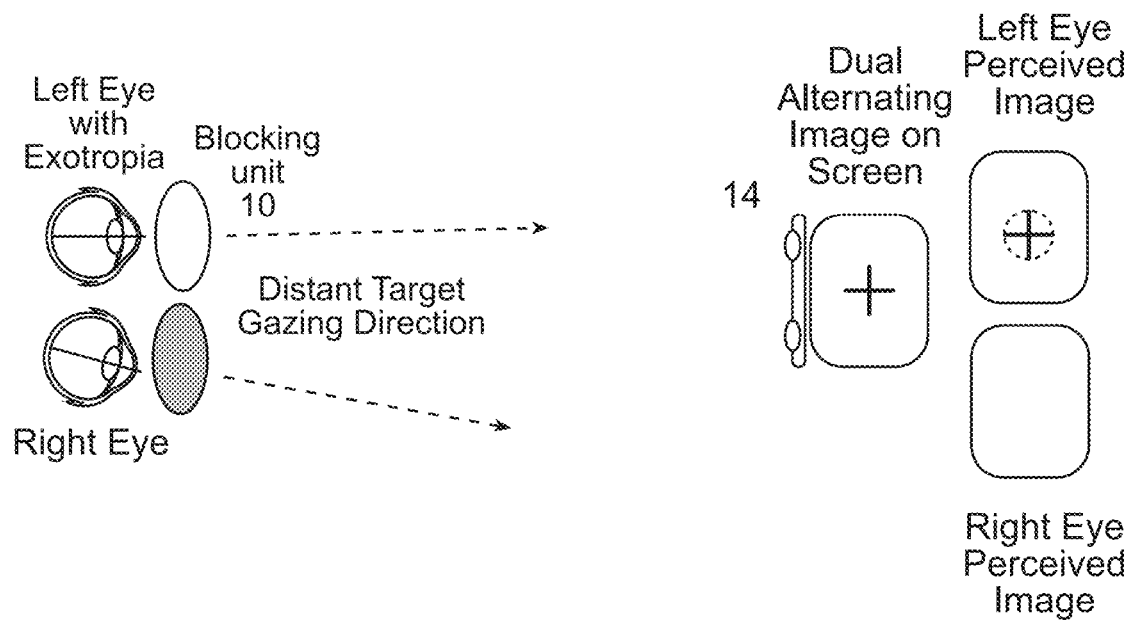

In step 3, illustrated in FIG. 3c, following binocular viewing (both shutters are opened), the two separate test targets continue to be displayed and coincide on the display unit 16. Blocking unit 10 becomes opaque for the right eye and prevents the right eye from seeing the image. While the blocked right eye sees nothing, the left eye of the patient instinctively turns inward (right), directs its gazing direction on the image, fixates and produces the perceived image shown in the figure. The camera unit data for the left eye is sent to the processing unit (not shown) which identifies the existence of an eye movement and determines whether there is a change (movement) in the position of the left eye. If there is a change in the position, the process continues as below.

Figure 3D:
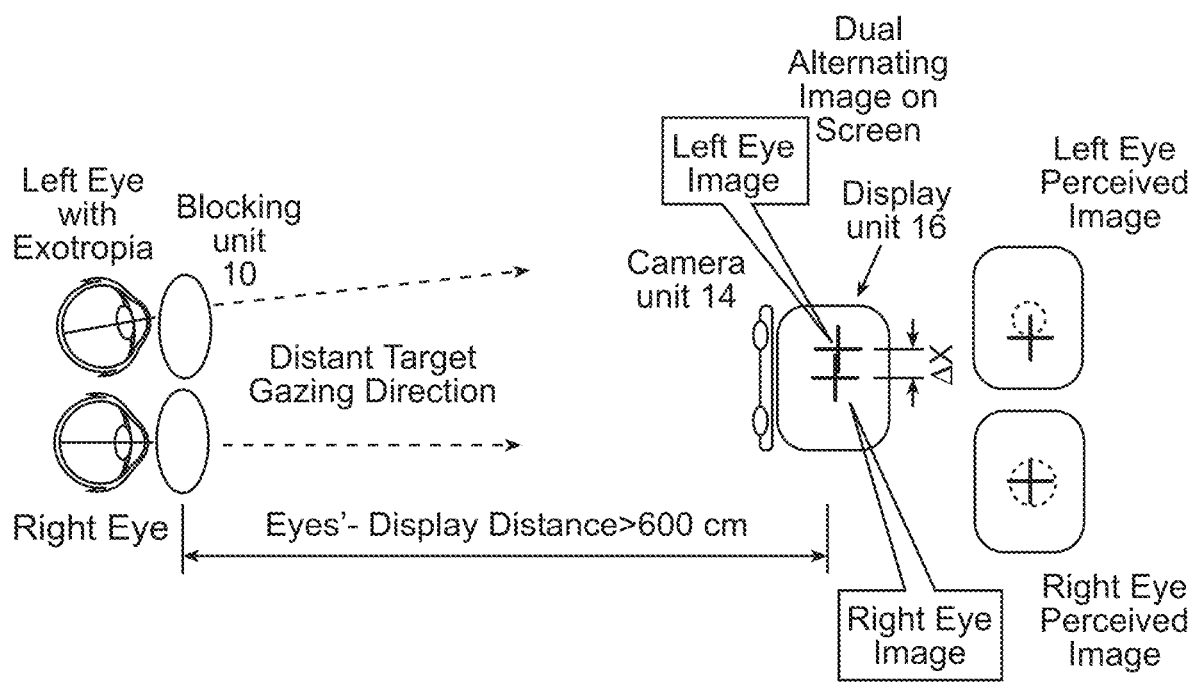

In step 4 illustrated in FIG. 3d, the target for the left eye is moved by ΔX (in relation to the previous target location) to the left side of the display unit 16 while the target for the right eye remains in the same location. Following binocular viewing (both shutters are opened), the right eye of the patient instinctively returns inward (left), directs its gazing direction on the image. The images perceived by the right and left eyes are shown in the figure. It should be noted that because of the new location of the target for the left eye, the perceived image by the left eye will be closer to the fovea than the perceived image than the fovea distance shown on FIG. 3a.

Figure 3E:
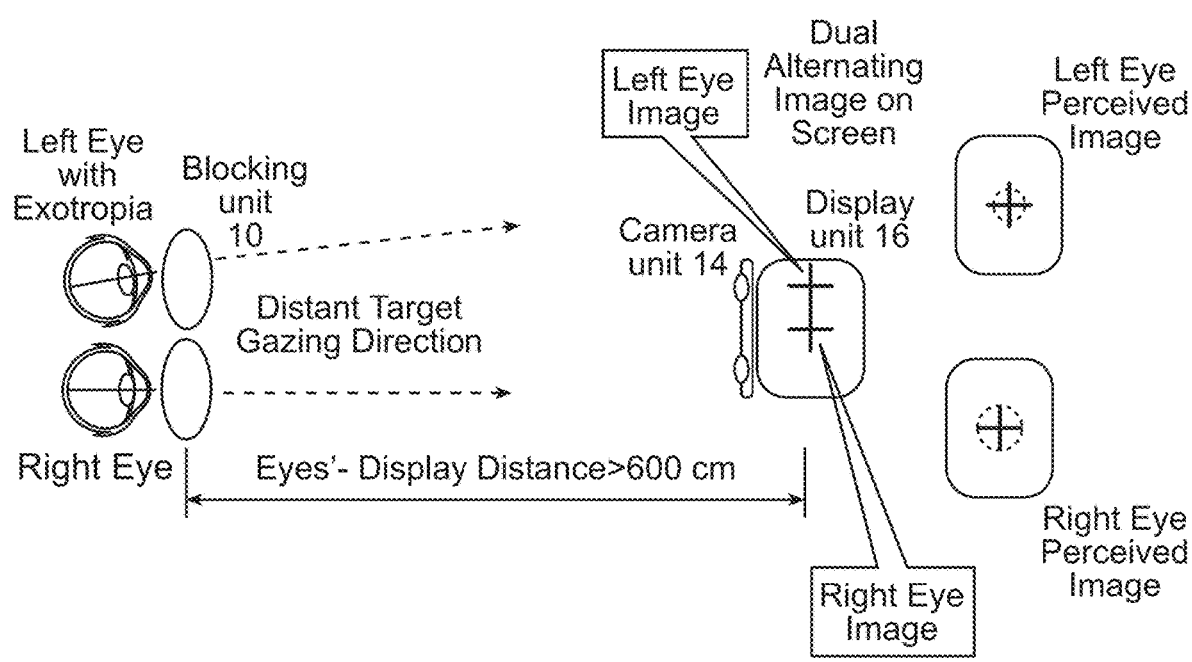

Steps 3 and 4 are then repeated continuously (while moving the target for the left eye more and more to the left side of the display with ΔX increments) and the differences between two consecutive position data get smaller, until there is no change detected in the left eye position. At that stage, as illustrated in FIG. 3e, the left target on the display unit 16 coincides with the deviated gazing direction of the left eye. Both eyes fixate on their corresponding targets and both targets fall on the fovea centers as seen in the figure. The strabismus deviation is then calculated. In this connection, it should be noted that although in this specific and non-limiting example, the target is displaced horizontally to determine strabismus deviation of a patient having exotropia, the target may be displaced additionally or alternatively vertically and/or rotationally. This enables to determine other ocular motility parameters such as esotropia, hypertropia or hypotropia.

Figure 4A:
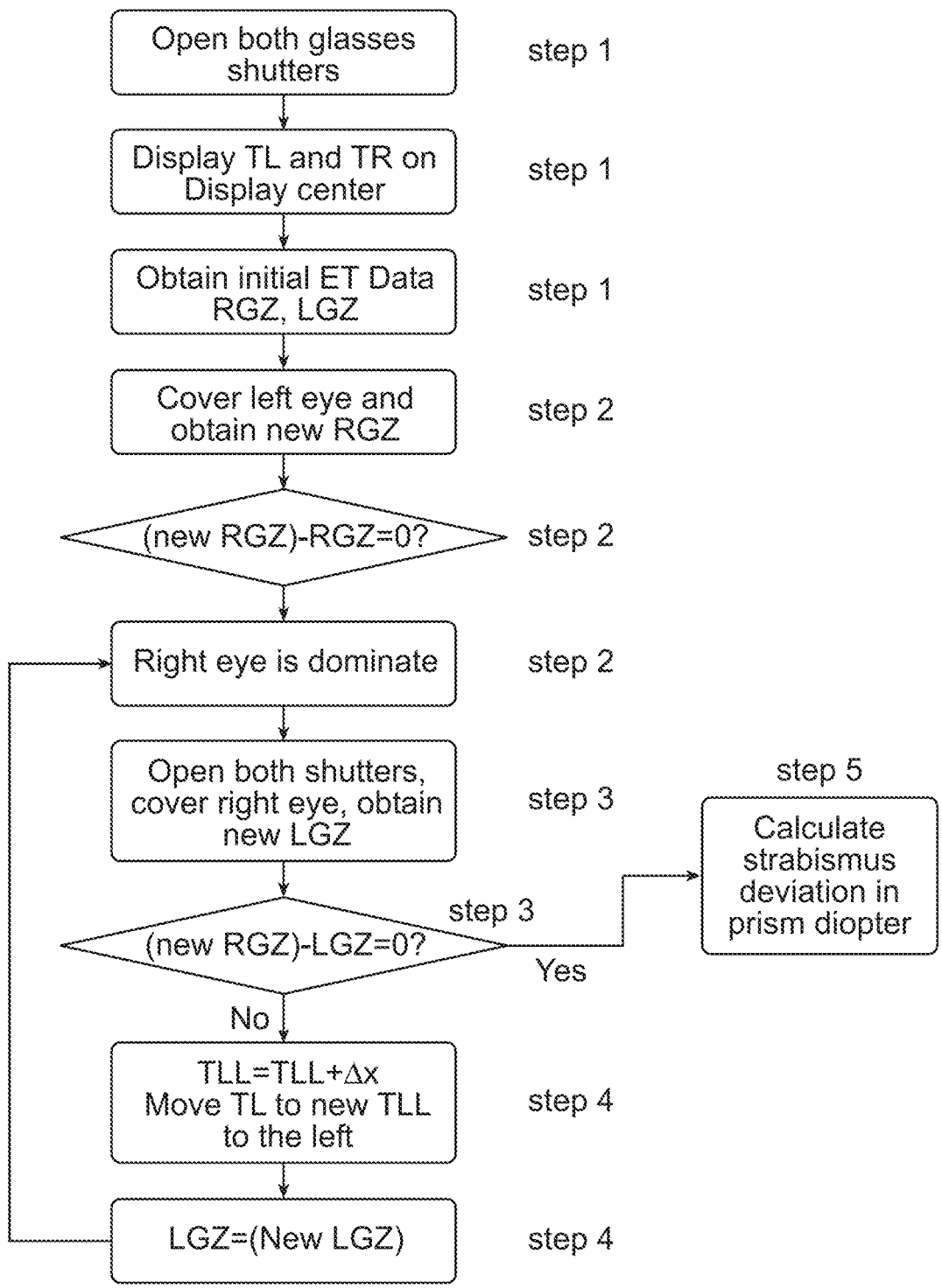
FIGS. 4a-4b are flow charts illustrating different examples of the method of the present invention.
Figure 4B:
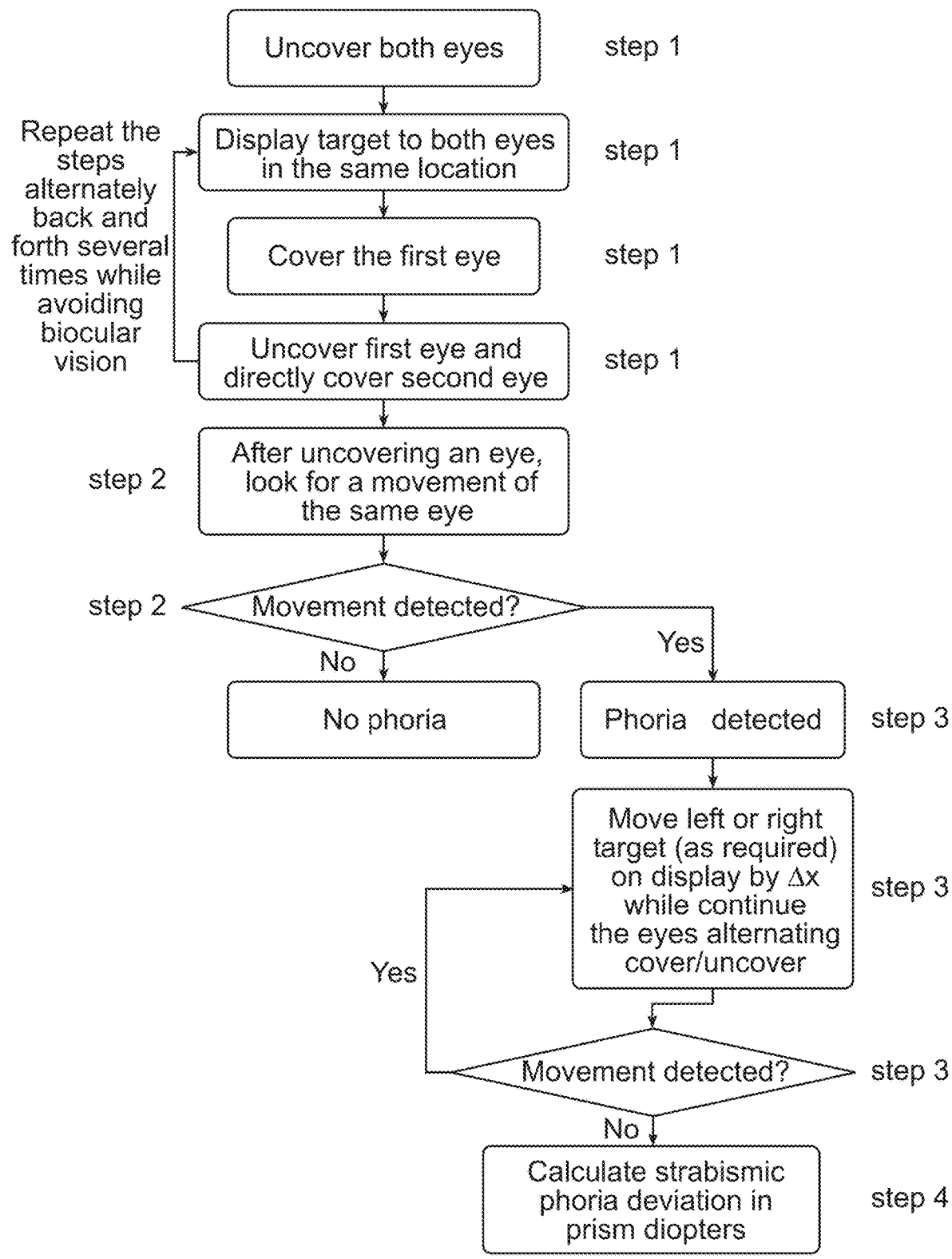

Reference is made to FIGS. 4a-4b representing examples of flow charts of the method according to some embodiments of the present invention. In the figures, the abbreviations are as follows: TL for Target for left eye, TLL for Left target location on display, TR for Target for right eye, ET for Eye Trackers, LGZ for Left eye gazing direction, RGZ for Right eye gazing direction, SPD for Strabismus deviation in prism diopters, TD for Final distance on display between TL and TR in centimeters and L for Distance between patient and display in centimeters.

Reference is made to FIG. 4a representing an example of a flow chart of the cover/uncover test method (for example, for heterotropia measurements) according to some embodiments of the present invention. Generally, the cover/uncover test is performed by covering one eye and monitoring the movement of the other eye. The right eye is assumed to be the non strabismic eye. Step 1 starts with both eyes not covered. Two test targets, one for each eye, coincide on the display unit and both alternating shutters are transparent. Then, initial data is obtained from the camera unit. More specifically, the camera unit (eye tracker) collects the data of each eye condition e.g. gazing direction. In step 2, the left eye is covered and the movement of the right eye is monitored. If no movement is detected, then the right eye is the non strabismic eye (according to the above assumption). In step 3, after presenting the targets that coincide in the initial phase of this step, the blocking unit becomes transparent for both eyes and then opaque for the right eye. The camera unit provides an image data indicative of the eye condition e.g. gazing direction of the left eye and the processing unit determines whether there is a change in the eye condition e.g. gazing direction of the left eye by comparing the image data acquired before. If there has been a change in gazing direction, then the process continues to step 4. The target for the left eye is slightly moved (e.g. by ΔX to the left side of the display unit as compared to the previous location of that target) while the target for the right eye remains in the same location. The camera unit provides an image data indicative of the eye condition e.g. gazing direction for the left eye and the processing unit determines the change in left eye position. Step 3 and 4 repeat themselves until no left eye movement is detected. At this stage, the target on the display unit coincides with the exact deviated gazing direction of the left eye. Both eyes fixate on the targets and both targets fall on the fovea centers as seen in FIG. 3d above.

For example, strabismus deviation is then calculated by using the following equation:

$$SPD = \frac{TD \times 100}{L}$$

When SPD is the strabismus deviation in prism diopter, TD is the final distance on the display unit between the separate targets for the separate eyes, and L is the distance between the patient and the display unit. Therefore, the distance between the two test targets determines the strabismus. In this formula. TD, L and SPD are in centimeter units. In this embodiment, the system of the present invention provides a difference between the eyes' gazing directions to thereby determine the gaze deviation angle of the strabismic eye.

In this embodiment, the system of the present invention provides a difference between the eyes' gazing directions to thereby determine the moment of zero difference. At that moment, the gaze deviation angle of the strabismic eye is determined by the targets' separation distance on the display.

It should be understood that in the technique of the present invention, the determination of the eye condition of each eye is performed concurrently with the display of the stimuli. Furthermore, the system is based on comparing differences of gazing data and not absolute gazing data and the calculations are made only after no gazing direction change is detected, so it does not depend at all on calibration. Furthermore, since the strabismus deviation is based only on simple measurements of distances, the results are extremely accurate compared to existing methods. This eliminates the need to calibrate the system before the stimulus is applied as performed in conventional systems using commercially available eye trackers. The calibration of the system for each patient and for each patient head position is time consuming and may provide inaccurate results since when the patient moves his head the calibration should be performed again. Such calibration is almost impossible to accomplish with young children. Furthermore, the technique of the present invention avoids the need to use prism lenses since the gazing deviation is performed using different images for each eye, on the screen.

It should also be understood that the technique of the present invention does not require a patient's cooperation, which is crucial for babies or even children. It requires only the patient's attention which can be achieved by using appropriate and interesting targets on the display.

A similar test is applied for the right eye if the left eye is the non strabismic eye.

It should be noted that the test described above in FIG. 4a is usually performed first. If no strabismus is found, the test described below in FIG. 4b can be performed.

Reference is made to FIG. 4b representing an example of a flow chart of an alternating cover test method (for example for heterophoria determination and measurements) according to some embodiments of the present invention. In step 1, two test targets, one for each eye, coincide on the display unit while both eyes are unblocked. Now, the blocking unit becomes opaque for the first eye, next the blocking unit becomes transparent to the first eye and opaque to the second eye without enabling binocular viewing in-between. Step 1 is repeated, for example, 5-10 times during 10-20 seconds, for allowing the visual system to disassociate the two eyes. In step 2, the camera unit generates image data of the first eye immediately after uncovering the first eye. In this specific and non-limiting example, the processing unit determines whether there is a change in the first eye condition (e.g. gazing direction) by comparing the image data acquired in step 2 and in step 1. If no change is detected, the camera unit generates image data of the second eye immediately after uncovering the second eye. The processing unit determines whether there is a change in the second eye condition e.g. gazing direction. If there is no change in the second eye condition as well, no phoria is detected. If a change in condition is detected in the first eye, phoria is detected and the process continues to step 3. In step 3, if a movement was detected in the first eye, the target for the first eye is slightly moved (e.g. by ΔX toward the direction of the first 34) eye position immediately after its uncovering) while the target for the second eye remains in the same location. If movement is detected for the second eye, the target for the second eye will be moved toward the direction of the second eye position while the target for the first eye will remain in the same location. Step 3 is then repeated. The camera unit generates image data immediately after uncovering the first eye. The processing unit determines whether there is a change in the first eye condition e.g. gazing direction. These steps are repeated sequentially by incrementing the target location on the display by ΔX. This process continues until the target on the display unit coincides with the exact deviated gazing direction of the first eye (Step 4). Both eyes fixate on the target and both targets fall on the fovea centers as seen in FIG. 3e above. No change is then measured by the processing unit for the first and second eyes and the ocular motility parameters are then calculated as above. In this way, there is provided a dynamic stimulus of the eye position when the target is displaced until no or minimal change in the eye condition is detected.

Figure 5A:
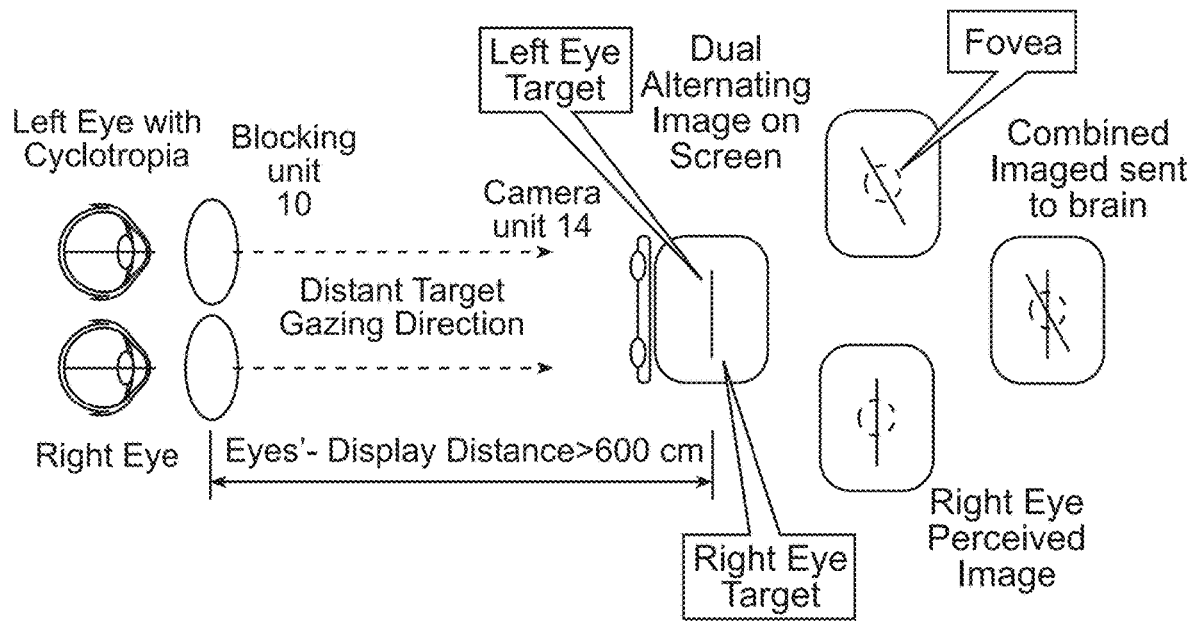
FIGS. 5a-5b illustrate an example of the system of the present invention together with images perceived on the retina of a Cyclo-Strabismic patient before and after the procedure completion respectively.
Figure 5B:
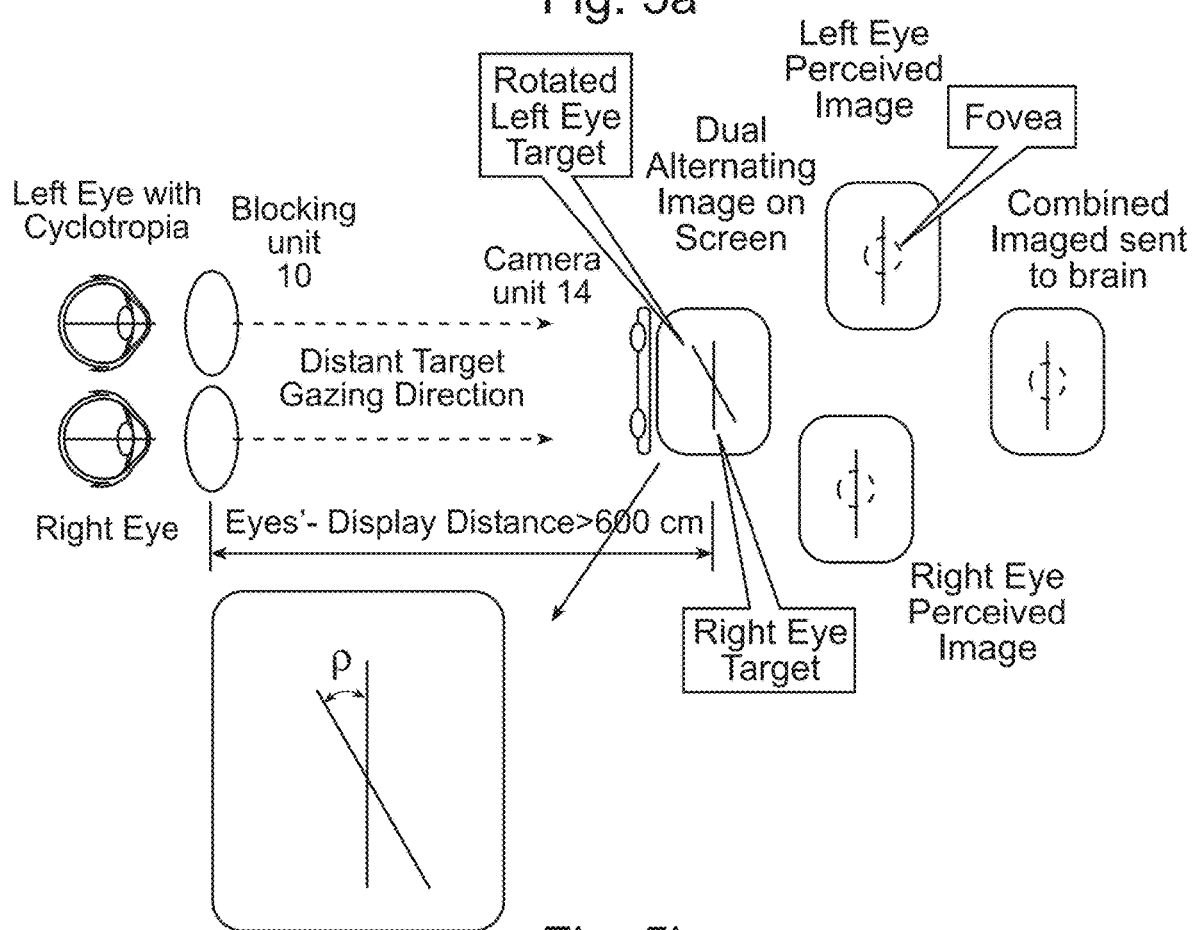

Reference is made now to FIGS. 5a-5b illustrating another embodiment of the present invention in which the technique is used for patients suffering from cyclotropia i.e. a strabismus in which, compared to the correct positioning of the eyes, there is torsion of one eye (or both) about the eye's visual axis. Consequently, the visual fields of the two eyes appear tilted relative to each other preventing the brain to fuse the two images into a single, stereoscopic image. As indicated above, the camera unit 14 generates image data indicative of an eye condition comprising at least one of horizontal gazing directions, vertical gazing directions and torsional rotations of the eyes. The processing unit (not shown) determines the torsion tilt of the eye. As shown in the figure, the two targets are displayed on the display unit at the same location and same tilt. In this case, the target is a horizontal line. The target for the tilted eye is then rotated axially until no eye rotation is detected by the camera unit 14 in similar steps and manners as described above but instead of moving the target by ΔX, the target is rotated by Δρ. The angle of the rotation ρ illustrated in FIG. 5b is indicative of the strabismic rotation in degrees.

According to another broad aspect of the present invention, there is provided a system for performing both far and near tests without changing the distance between the display unit and the patient. Usually, near field tests are performed at 33 to 40 cm distance between the target and the patient, while far field tests are performed at least 300 cm distance between the target and the patient.

Figure 6:
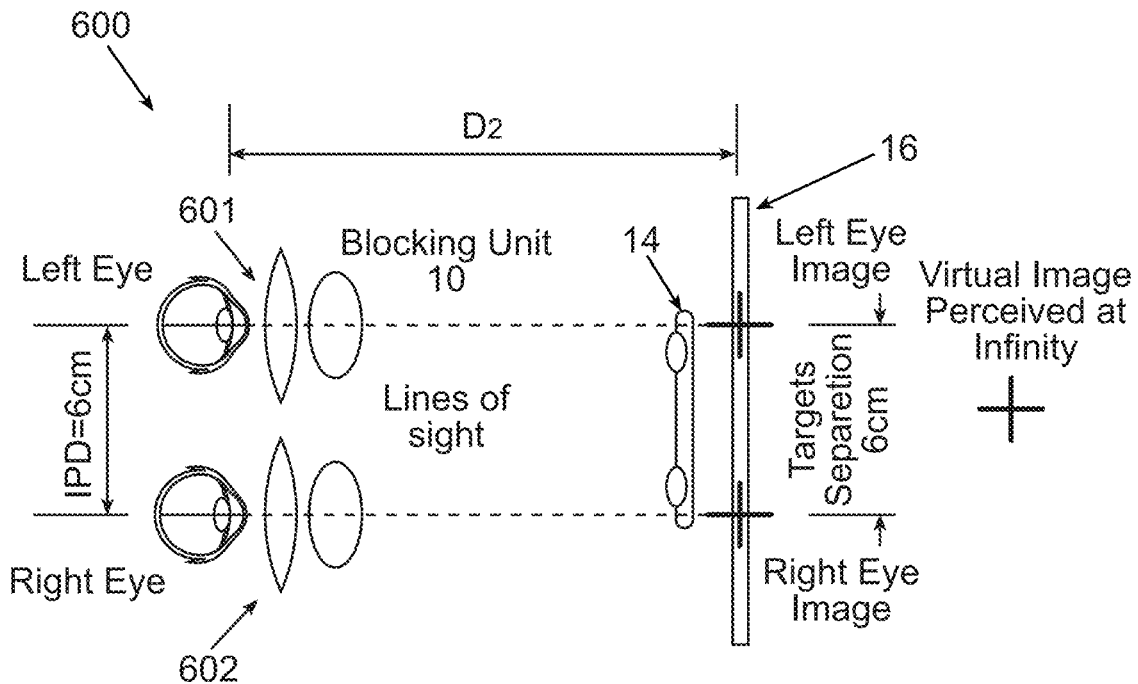
FIG. 6 illustrates an example of the system of the present invention for far field configuration.
Figure 7:
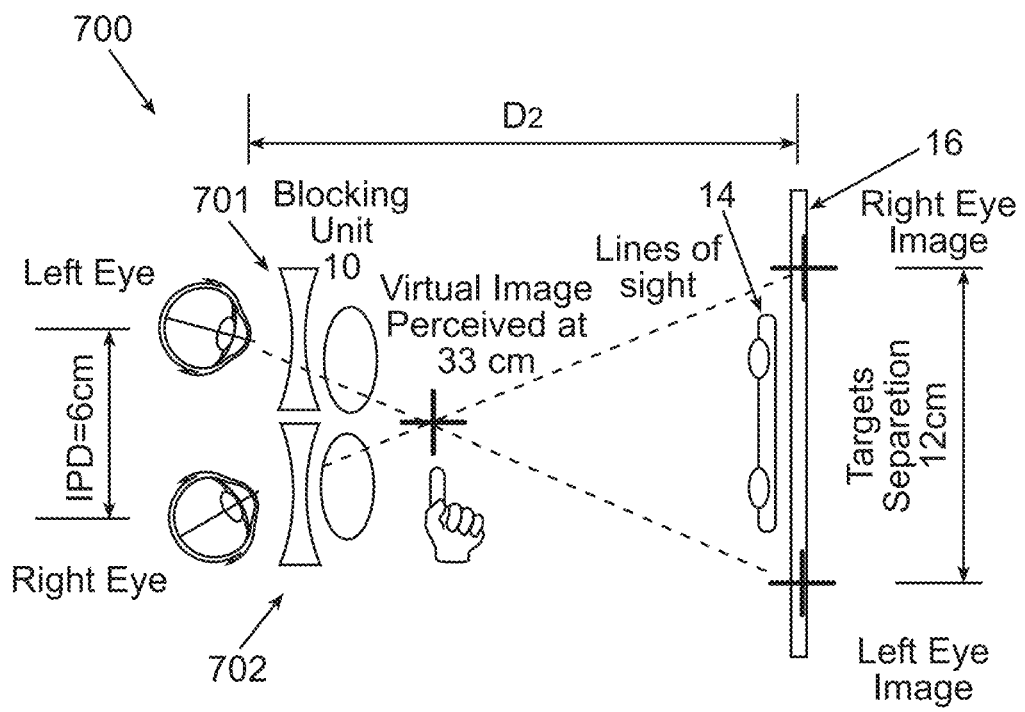
FIG. 7 illustrates an example of the system of the present invention for near field configuration.

Reference is made to FIG. 6 and FIG. 7 schematically representing the ability of the system of the present invention to perform both far and near tests illustrated in FIG. 6 and FIG. 7 respectively on a single screen at a fixed location. For the sake of comparison, it may be assumed that the patient has normal vision in the sense of far and near visual acuity and far and near vergence capability. The non-limiting example illustrated in FIG. 6 shows a setup configuration 600 aimed at measuring distant vision strabismus deviation of a patient. The display unit 16 is located at a distance D2 being, for example, 100 cm away from the patient. The targets for each respective eye are displayed on the display unit at about the Interpupillary Distance (IPD) to keep the gazing directions of the two eyes parallel, as requited for far field vision. The targets are displayed on the display unit 16 at a distance of 6 cm (as for this example a typical IPD) as shown in the figure. This ensures that the gazing directions of the two eyes are parallel, as required for far vision. In order to present normal targets in far field, no accommodation is required i.e. the eyes should focus on infinity. In this case, both eyes focus on far away targets and both gazing directions are parallel. The system 600 also comprises focusing optics comprising at least two optical lenses 601 and 602 having a certain focal point each being placed in front of each eye. Lenses 601 and 602 may be convex lenses. The focus optics is configured and operable to receive an image from the display unit and project the image to each eye in such a way so that the eye sees the target at infinity. The lens thus creates a virtual target located at infinity. This ensures that the accommodation of the two eyes is at a far field, as required for far vision.

The term "virtual" hereinafter refers to a target located at a focal plane different from the display unit. Although, for the sake of simplicity, the focusing optics is represented as a separate physical element from the blocking unit 10, the focus optics may be integrated in the blocking unit 10 to form a single physical element.

A similar system can be used for various distances of the display unit to the patient. In a specific and non-limiting example, an eyes-display unit distance of about 100 cm, an IPD of about 6 cm, +1.00 diopter lenses should be used, for a distance of about 50 cm, +2.00 diopter lenses should be used and for a distance of about 33 cm, +3.00 diopter lenses should be used and the virtual target would be projected accordingly as being in infinity. In all these cases, the spaced-apart targets are displayed on the display unit at a distance of about 6 cm.

Reference is made to FIG. 7 representing a possible configuration of the system of the present invention for near field examination. The non-limiting example illustrated in FIG. 7 shows a setup configuration 700 aimed at measuring near vision strabismus deviation of a patient. The display unit 16 is located at a distance D2 being, for example, 100 cm away from the patient. The targets for each respective eye are displayed on the display unit as follows: the target for the left eye is located at the right side of the display unit and vice versa. The spaced-apart targets are displayed on the display at a certain distance but in opposite direction as in the previous configuration illustrated for example in FIG. 6. This ensures that the gazing directions of the two eyes are converged as required for near vision at an appropriate distance.

In order to present normal targets in near field, the eyes should accommodate. i.e. the eyes should focus on a near field. In this case, both eyes focus on near targets and both gazing directions converge at the required near distance e.g. 30 centimeters. The system 700 also comprises focusing optics comprising at least two optical lenses 601 and 602 having a certain focal point each being placed in front of each eye. Lenses 701 and 702 may be concave lenses. The focusing optics is configured and operable to receive an image from the display unit and project the image to each eye in such a way so that the eye sees the target at a near field. The lens thus creates a virtual target located at a near field. This ensures that accommodation of the two eyes is at a near field, as required for near vision.

As described above with respect to FIG. 6, the distance between the patient's eyes and the display may be varied and the focal point of the focusing optics, as well as the distance between the targets, should be selected accordingly. For example, for a distance of about 100 cm away between the display and the patient, the focusing optics should be −2.00 diopter (concave lenses). It should be understood that for the eye to see a target at 33 cm, a −3.00 diopter lens (in order to force +3.00 diopter of accommodation) should be used and a +1.00 diopter lens (to compensate for the accommodation needed for a 1-meter distance of the screen) should be added which sums together to −2.00 diopter lens. The distance between the targets should be about 12 cm apart to force eye convergence at about 33 cm. For a 50 cm eye-display distance, a −1.00 diopter lens should be used (−3.00 and +2.00) and the targets should be separated by about 9 cm. In this connection, it should be noted that increasing the relative distance between the 34) targets on the display decreases the distance between the virtual target and the patient and vice versa.

It should also be noted that for near field simple calculation, a direct eye-display distance of 100 cm was taken into account. However, more accurate calculations can be performed as the distance between patient eyes and displayed target is not exactly 100 cm as in this example. Such calculations may be made by using simple trigonometric relations such that a more accurate distance is calculated as follows:

$$D=3+(100^2+6^2)^{0.5}=-103.2 \text{ cm.}$$

In some embodiments, a real target can be inserted at the appropriate distance of the near field vision, if the patient has difficulty in converging his eyes to the right degree. As illustrated in FIG. 7, this target may be a finger inserted into his line of sight.

As described above, in some embodiments, the system may comprise personal correction optics. The corrective lenses may be combined with the focusing optics described in FIGS. 6 and 7. For example, if a person has a far field correction lens of +2.50 diopter and addition of +2.00 diopter for near vision, the combined lens can be as follows:

For far field example: +1.00+2.50=+3.50 diopter

For near field example: +1.00−3.00+2.00+2.50=+2.50 diopter

Figure 8:
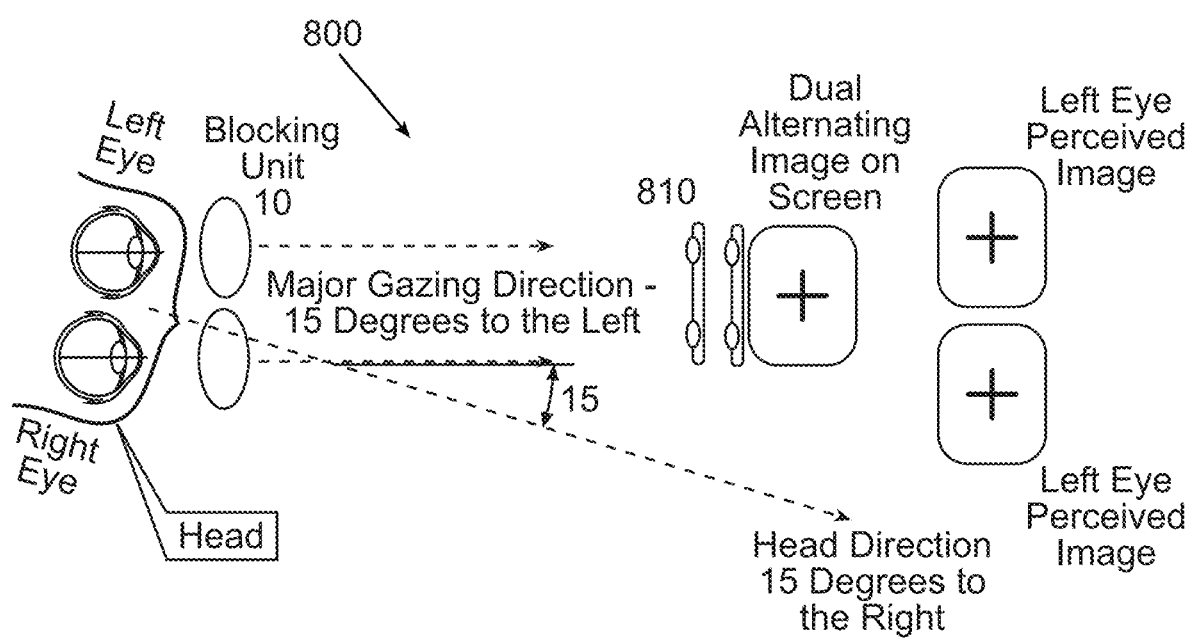
FIG. 8 illustrates another example of the system of the present invention.

Reference is made to FIG. 8 illustrating another configuration of the system of the present invention. Typically, strabismus tests should be performed in different major gazing directions (head positions). In the above-described examples, it was assumed that the patient is looking straight ahead. This major gazing direction angle may be defined as 0 degrees. As illustrated in the figure, if the patient rotates his head at a certain angle α to the right, his major gazing direction will be α to the left. The system 800 comprises a head position detector 810 configured to determine a head direction. The head position detector 810 may be a separate element (commercially available) and may be integrated with the camera or the processing unit. The head position data can be inserted to the system manually. The processing unit (not shown) is connected via wire or may be wireless to the head position detector 810 and registers the ocular motility parameters accordingly. This enables to determine ocular motility parameters for different major gazing directions.

It should be noted that if virtual targets as described above are used for strabismus deviation tests, the initial locations of the virtual targets on the display, instead of coinciding in the middle of the display, will be located at a certain distance from each other, as shown in FIGS. 6 and 7. The patient perception of the initial locations will be as the targets coincide. From there on, the targets will move according to the same processing, and strabismus calculations use those locations appropriately.

The invention claimed is:

1. A method for measuring ocular motility of a patient and ocular motion abnormality comprising:
 (a) simultaneously displaying one target for the first eye and one target for the second eye of the patient;
 (b) collecting at least one image indicative of the first orientation;
 (c) determining a first orientation of the first eye;
 (d) blocking a field of view of the second eye;
 (e) collecting at least one image indicative of a second orientation of the first eye;
 (f) determining a second orientation of the first eye;
 (g) identifying an existence of an eye movement of the first eye and determining whether there is a change in the orientation of the first eye as a result of said blocking;
 (h) if a change is determined, unblocking the field of view of the second eye, displaying the target for the first eye;
 (i) repeating steps (b)-(h), until no change in the orientation of at least the first eye is measure;
 displaying at least two targets creating a virtual target at a required distance from the patient; and measuring the ocular motility and ocular motion abnormality of the first eye.

2. The method of claim 1, further comprising varying said required distance to thereby enable keeping a distance between a display unit, configured to display the two targets, and a patient fixed, while varying a virtual target distance from the patient.

3. The method of claim 1, further comprising changing the distance between the two targets on the display.

4. The method of claim 1, further comprising controlling an accommodation state of the eyes by providing focusing optics.

5. The method of claim 1, further comprising selecting a distance between the display unit and the patient to be in the range of about 30 cm to 700 cm.

* * * * *